(12) United States Patent
Park et al.

(10) Patent No.: US 11,850,095 B2
(45) Date of Patent: Dec. 26, 2023

(54) ULTRASOUND IMAGING DEVICE AND METHOD USING POSITION AND POSTURE TRACKING OF PROBE OF ULTRASOUND SCANNER

(71) Applicant: DECASIGHT CORPORATION, Seoul (KR)

(72) Inventors: Byung Joon Park, Seoul (KR); Soo Ho Choi, Seoul (KR); Tae Hyun Kim, Seoul (KR)

(73) Assignee: DECASIGHT CORPORATION, Seoul (KR)

( * ) Notice: Subject to any disclaimer, the term of this patent is extended or adjusted under 35 U.S.C. 154(b) by 44 days.

(21) Appl. No.: 17/596,851

(22) PCT Filed: Apr. 29, 2020

(86) PCT No.: PCT/KR2020/005696
§ 371 (c)(1),
(2) Date: Dec. 20, 2021

(87) PCT Pub. No.: WO2020/256276
PCT Pub. Date: Dec. 24, 2020

(65) Prior Publication Data
US 2022/0313215 A1      Oct. 6, 2022

(30) Foreign Application Priority Data

Jun. 21, 2019   (KR) .................. 10-2019-0073997

(51) Int. Cl.
*A61B 8/00*       (2006.01)
*G06T 7/70*       (2017.01)
*G06T 17/20*      (2006.01)

(52) U.S. Cl.
CPC ............ *A61B 8/466* (2013.01); *A61B 8/4263* (2013.01); *G06T 7/70* (2017.01); *G06T 17/20* (2013.01);
(Continued)

(58) Field of Classification Search
None
See application file for complete search history.

(56) References Cited

U.S. PATENT DOCUMENTS

2016/0242744 A1    8/2016   Mihailescu et al.
2018/0308247 A1*  10/2018   Gupta ................... G01N 29/44
(Continued)

FOREIGN PATENT DOCUMENTS

JP          2014-236998 A       12/2014

OTHER PUBLICATIONS

KR Office Action for 10-2019-0073997, dated Nov. 4, 2020.
International Search Report for PCT/KR2020/005696, dated Nov. 19, 2020.

*Primary Examiner* — Frank S Chen
(74) *Attorney, Agent, or Firm* — Sughrue Mion, PLLC

(57) ABSTRACT

Disclosed is an ultrasonic image presentation device comprising: an ultrasonic scanner having a probe which is a part coming into direct contact with an object and a marker; a photographing unit configured to photograph the marker; an ultrasonic image presentation unit configured to acquire an ultrasonic image as a two-dimensional depth cross-sectional image for a part coming into contact with the probe of the ultrasonic scanner, estimate a position and posture of the marker in a three-dimensional image on the basis of an image photographed by the photographing unit; estimate a position and posture of the probe in the three-dimensional image from the estimated marker position and posture information, create a point cloud by converting pixels of the ultrasonic image into points of the three-dimensional image (Continued)

on the basis of the estimated probe position and posture information, and restore the three-dimensional ultrasonic image on the basis of the created point cloud; and a display unit configured to display the three-dimensional ultrasonic image restored by the ultrasonic image presentation unit. It is possible to provide a three-dimensional ultrasonic image simply and easily with lower cost.

10 Claims, 13 Drawing Sheets

(52) U.S. Cl.
CPC ............... *G06T 2207/10028* (2013.01); *G06T 2207/30204* (2013.01)

(56) References Cited

U.S. PATENT DOCUMENTS

| | | | |
|---|---|---|---|
| 2019/0318484 A1* | 10/2019 | Dougherty | ............ G06T 7/0012 |
| 2022/0079561 A1* | 3/2022 | Takahashi | ............ A61B 8/5246 |

* cited by examiner

ULTRASOUND IMAGING DEVICE AND METHOD USING POSITION AND POSTURE TRACKING OF PROBE OF ULTRASOUND SCANNER

CROSS REFERENCE TO RELATED APPLICATIONS

This application is a National Stage of International Application No. PCT/KR2020/005696 filed Apr. 29, 2020, claiming priority from Korean Patent Application No. 10-2019-0073997, filed in the Korean Patent Office on Jun. 21, 2019, the entire contents of which are incorporated herein by reference.

BACKGROUND OF THE INVENTION

Field of the Invention

The present invention relates to an ultrasonic image presentation technology using an ultrasonic scanner. More specifically, the present invention relates to a real-time three-dimensional ultrasonic image restoration technology using position and posture tracking of an ultrasonic scanner probe, that is, a device and method for accurately tracking the position and posture of the probe, which is a part coming into direct contact with a patient's body among components of the two-dimensional ultrasonic scanner, and restoring a sonographic image of an internal organ of a human body in real time in a three-dimensional format.

Description of Related Art

In general, an ultrasonic system is a system that examines an internal condition of a target object by emitting an ultrasonic signal to the object to be inspected on the basis of the piezoelectric effect of a transducer, which is a probe, receiving the resulting ultrasonic signal reflected and returned from a discontinuous surface of the object, converting the received ultrasonic signal into an electric signal, and outputting it to a predetermined imaging device. Such an ultrasonic system is widely employed for medical diagnosis, non-destructive testing, underwater navigation devices, and the like.

That is, the ultrasonic diagnostic device is mainly used for medical purposes, such as observing the inside of the object, detecting a foreign substance, and measuring an injury, by irradiating the ultrasonic signal generated from the transducer of the probe from a body surface of the object toward a target site, receiving information of the reflected ultrasonic signal (ultrasonic echo signal), and obtaining a tomographic image of soft tissues or blood flow for an internal part of the object without invasiveness.

Such an ultrasonic diagnostic device is compact and inexpensive, compared to other diagnostic imaging devices such as an X-ray diagnostic device, an X-ray computerized tomography (CT) scanner, a magnetic resonance image (MRI) device, and a nuclear medicine diagnostic device, and can provide imaging in real time. In addition, the ultrasonic diagnostic device ensures no radiation exposure and high safety advantageously. Therefore, it is widely used along with other diagnostic imaging devices.

As described above, the ultrasonic scanner is a device that acquires a two-dimensional depth cross-sectional image at a specific position on the basis of the difference in the reflection time of ultrasound. Unlike other imaging devices such as a CT scanner or MRI, the ultrasonic scanner is advantageous in that information can be obtained in real time, and there is no radiation exposure caused by X-ray radiation or the like.

Recently, a three-dimensional ultrasonic imaging device using such a two-dimensional ultrasonic scanner has been widely used, but most of them have a limitation in that three-dimensional restoration is possible only for a local region in a fixed position.

SUMMARY OF THE INVENTION

In order to address the problems or disadvantages described above, the present invention provides a device and method for ultrasonic image presentation, capable of tracking a position and posture of the probe by using separate external cameras and accurately restoring and providing a wide range of three-dimensional models on the basis of the tracked position and posture of the probe.

The object of the present invention is not limited to those described above, and other unmentioned objects would become apparent to those skilled in the art would by reading the following description.

In order to achieve the objects described above, according to an aspect of the present invention, there is provided an ultrasonic image presentation device comprising: an ultrasonic scanner having a probe which is a part coming into direct contact with an object and a marker; a photographing unit configured to photograph the marker; an ultrasonic image presentation unit configured to acquire an ultrasonic image as a two-dimensional depth cross-sectional image for a part coming into contact with the probe of the ultrasonic scanner, estimate a position and posture of the marker in a three-dimensional image on the basis of an image photographed by the photographing unit; estimate a position and posture of the probe in the three-dimensional image from the estimated marker position and posture information, create a point cloud by converting pixels of the ultrasonic image into points of the three-dimensional image on the basis of the estimated probe position and posture information, and restore the three-dimensional ultrasonic image on the basis of the created point cloud; and a display unit configured to display the three-dimensional ultrasonic image restored by the ultrasonic image presentation unit.

The ultrasonic image presentation unit may create a three-dimensional mesh from the point cloud created on the basis of information on points of the three-dimensional image created as the probe moves, and the three-dimensional ultrasonic image may be restored on the basis of the created three-dimensional mesh.

The photographing unit may have a single camera, the marker may be a two-dimensional image marker, and the ultrasonic image presentation unit may search for the two-dimensional image marker from the image photographed by the single camera and estimate the position and posture of the two-dimensional image marker.

The photographing unit may include a multi-camera set having a plurality of cameras provided in a plurality of places, the marker may be a bar type marker formed in a bar shape, and the ultrasonic image presentation unit may search for the bar type marker from the images photographed by the multi-camera set and estimate the position and posture of the bar type marker.

The ultrasonic image presentation unit may estimate the position and posture of the probe by using the position and posture information of the marker and information on a relative distance and a relative angle between the marker and the probe measured in advance.

The ultrasonic image presentation unit may create a point cloud by converting pixels of the ultrasonic image into points of a three-dimensional image depending on a relative distance from the position of the probe.

According to another aspect of the present invention, there is provided an ultrasonic image presentation method using an ultrasonic image presentation device provided with an ultrasonic scanner having a probe which is a part coming into direct contact with an object and a marker, a photographing unit for photographing the marker, an ultrasonic image presentation unit, and a display unit, the method comprising: acquiring an ultrasonic image which is a two-dimensional depth cross-sectional image for a part coming into contact with the probe of the ultrasonic scanner; estimating a position and posture of the marker in a three-dimensional image on the basis of the image photographed by the photographing unit; estimating a position and posture of the probe in the three-dimensional image on the basis of the estimated position and posture information of the marker; creating a point cloud by converting pixels of the ultrasonic image into points of the three-dimensional image on the basis of the estimated position and posture information of the probe; and restoring the three-dimensional ultrasonic image on the basis of the created point cloud and displaying the restored three-dimensional ultrasonic image on the display unit.

The ultrasonic image presentation unit may create a three-dimensional mesh from a point cloud created from information on points of the three-dimensional image created as the probe moves, and the three-dimensional ultrasonic image may be restored on the basis of the created three-dimensional mesh.

The photographing unit may include a single camera, the marker may be a two-dimensional image marker, and the ultrasonic image presentation unit may search for the two-dimensional image marker from the image photographed by the single camera and estimate the position and posture of the two-dimensional image marker.

The photographing unit may include a multi-camera set provided with a plurality of cameras placed in a plurality of positions, the marker may be a bar type marker formed in a bar shape, and the ultrasonic image presentation unit may search for the bar type marker from the images photographed by the multi-camera set and estimate the position and posture of the bar type marker.

The ultrasonic image presentation unit may estimate the position and posture of the probe by using position and posture information of the marker and information on a relative distance and a relative angle between the marker and the probe measured in advance.

The ultrasonic image presentation unit may create a point cloud by converting pixels of the ultrasonic image into points of a three-dimensional image depending on a relative distance from the position of the probe.

According to the present invention, it is possible to restore and provide a three-dimensional ultrasonic image in real time from a two-dimensional ultrasonic image by tracking a position and posture of the probe of the ultrasonic scanner. Therefore, it is possible to simply and easily provide a three-dimensional ultrasonic image with lower cost.

According to the present invention, it is possible to enable three-dimensional observation for internal parts in a specific region under a medical environment in real time. Therefore, it is possible to provide an intuitive help in accurately diagnosing and treating a complex and difficult anatomical abnormality in a human body.

BRIEF DESCRIPTION OF THE DRAWINGS

The foregoing and additional features and characteristics of this disclosure will become more apparent from the following detailed description considered with reference to the accompanying drawings, wherein.

DETAILED DESCRIPTION OF THE INVENTION

Figure 1:
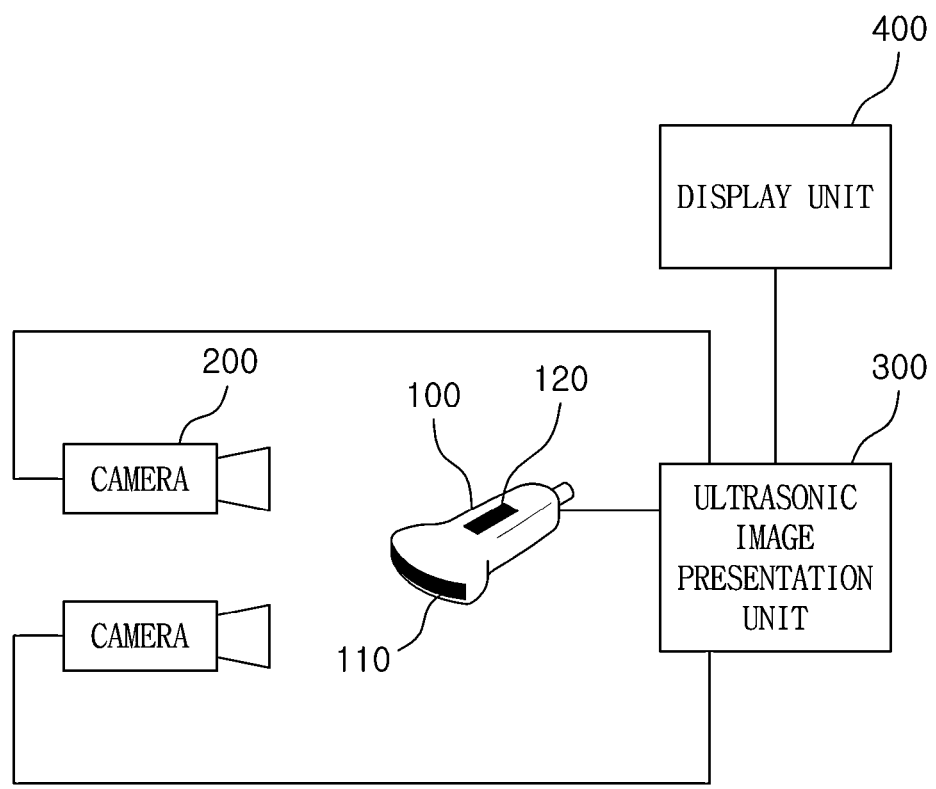
FIG. 1 is a block diagram illustrating a configuration of an ultrasonic image presentation device according to an embodiment of the present invention.

According to the present invention, an ultrasonic image presentation device includes: an ultrasonic scanner having a probe which is a part coming into direct contact with an object and a marker; a photographing unit configured to photograph the marker; an ultrasonic image presentation unit configured to acquire an ultrasonic image as a two-dimensional depth cross-sectional image for a part coming into contact with the probe of the ultrasonic scanner, estimate a position and posture of the marker in a three-dimensional image on the basis of an image photographed by the photographing unit; estimate a position and posture of the probe in the three-dimensional image from the estimated marker position and posture information, create a point cloud by converting pixels of the ultrasonic image into points of the three-dimensional image on the basis of the estimated probe position and posture information, and restore the three-dimensional ultrasonic image on the basis of the created point cloud; and a display unit configured to display the three-dimensional ultrasonic image restored by the ultrasonic image presentation unit.

Hereinafter, preferred embodiments of the invention will be described in detail with reference to the accompanying drawings. It is noted that like reference numerals denote like elements throughout overall drawings. In addition, descriptions of well-known apparatus and methods may be omitted so as to not obscure the description of the representative embodiments, and such methods and apparatus are clearly within the scope and spirit of the present disclosure. The terminology used herein is only for the purpose of describing particular embodiments and is not intended to limit the invention. As used herein, the singular forms "a," "an," and "the" may be intended to include the plural forms as well, unless the context clearly indicates otherwise. It is further to be noted that, as used herein, the terms "comprises," "comprising," "include," and "including" indicate the presence of stated features, integers, steps, operations, units, and/or components, but do not preclude the presence or addition of one or more other features, integers, steps, operations, units, and/or components, and/or combination thereof.

Unless specified otherwise, all terminologies used herein including technical or scientific terminologies have the same meanings as those generally appreciated by a person ordinarily skill in the art to which the present invention pertains. Terminologies defined in typical dictionaries should be construed to have meanings matching those described in the context of the related art, and should not be construed as being abnormal or excessively formal unless defined apparently herein.

The present invention will now be described with reference to the accompanying drawings, in which like reference numerals denote like elements throughout the entire specification, and they will not be repeatedly described intentionally. In the following description, any specific word or sentence for the related art will not be provided for simplicity purposes if it unnecessarily obscures the subject matter of the invention.

FIG. 1 is a block diagram illustrating a configuration of the ultrasonic image presentation device according to an embodiment of the present invention.

Referring to FIG. 1, the ultrasonic image presentation device according to the present invention has an ultrasonic scanner 100, a camera 200, an ultrasonic image presentation unit 300, and a display unit 400.

The ultrasonic scanner 100 is provided with a probe 110, which is a part coming into direct contact with an object, and the marker 120.

The photographing unit 200 photographs the marker 120. According to the present invention, the photographing unit 200 may be a single camera or a multi-camera set including a plurality of cameras.

The ultrasonic image presentation unit 300 acquires an ultrasonic image, which is a two-dimensional depth cross-sectional image for a part coming into contact with the probe 110 of the ultrasonic scanner 100. In addition, the position and posture of the marker 120 in the three-dimensional image is estimated on the basis of the image taken from the photographing unit 200.

The ultrasonic image presentation unit 300 estimates the position and posture of the probe 110 in the three-dimensional image from the estimated position and posture information of the marker 120. In addition, from the estimated position and posture information of the probe 110, a point cloud is created by converting the pixels of the ultrasonic image into points of a three-dimensional image, and a three-dimensional ultrasonic image is restored on the basis of the created point cloud.

According to an embodiment of the present invention, the ultrasonic image presentation unit 300 may create a three-dimensional mesh from the point cloud created on the basis of the point information of the three-dimensional image created as the probe 110 moves. In addition, on the basis of the created three-dimensional mesh, the three-dimensional ultrasonic image may be restored.

The display unit 400 is configured to display the three-dimensional ultrasonic image restored by the ultrasonic image presentation unit 300. For example, the display unit 400 may be implemented as an LCD, LED, or the like.

Figure 5:
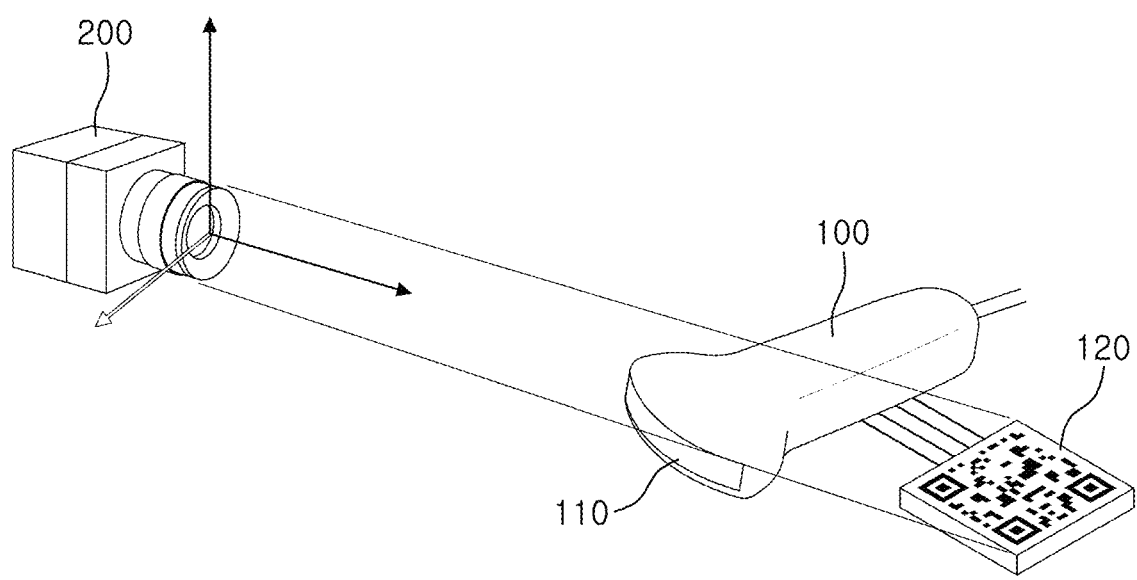
FIG. 5 illustrates a single camera and a two-dimensional image marker according to an embodiment of the present invention.

FIG. 5 illustrates a single camera and a two-dimensional image marker according to an embodiment of the present invention.

Referring to FIG. 5, according to an embodiment of the present invention, the photographing unit 200 may be configured as a single camera, and the marker 120 may be implemented as a two-dimensional image marker. In this case, the ultrasonic image presentation unit 300 may search for a two-dimensional image marker from the image taken by the single camera, and estimate the position and posture of the two-dimensional image marker.

Figure 6:
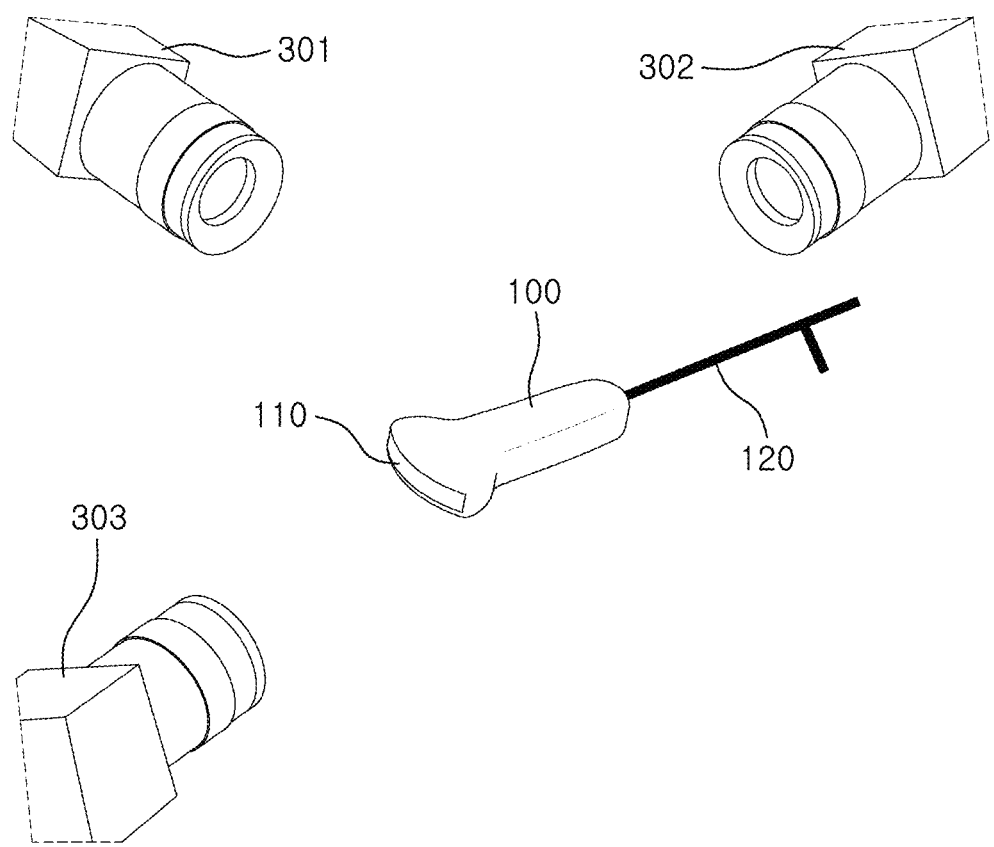
FIG. 6 illustrates a multi-camera set and a bar type marker according to another embodiment of the present invention.

FIG. 6 illustrates a multi-camera set and a bar type marker according to another embodiment of the present invention.

Referring to FIG. 6, the photographing unit 200 according to another embodiment of the present invention may be configured as a multi-camera set including a plurality of cameras installed at a plurality of places, and the marker 120 may be implemented as a bar type marker formed in a bar shape. The bar type marker may be in the form of a line segment that can be identified in the longitudinal direction of the bar shape. The bar type marker may be implemented as a laser beam having a thin straight line segment to increase the precision, or may be implemented as a bar type solid material having a straight line segment.

In this case, the ultrasonic image presentation unit 300 may search for a bar type marker from the image taken from the multi-camera set, and estimate the position and posture of the bar type marker.

The ultrasonic image presentation unit 300 may estimate the position and posture of the probe 110 by using the position and posture information of the marker 120 and information on the relative distance and relative angle between the marker 120 and the probe 110 measured in advance.

The ultrasonic image presentation unit 300 may create a point cloud by converting pixels of the ultrasonic image into points of the three-dimensional image depending on the relative distance from the position of the probe 110.

Figure 2:
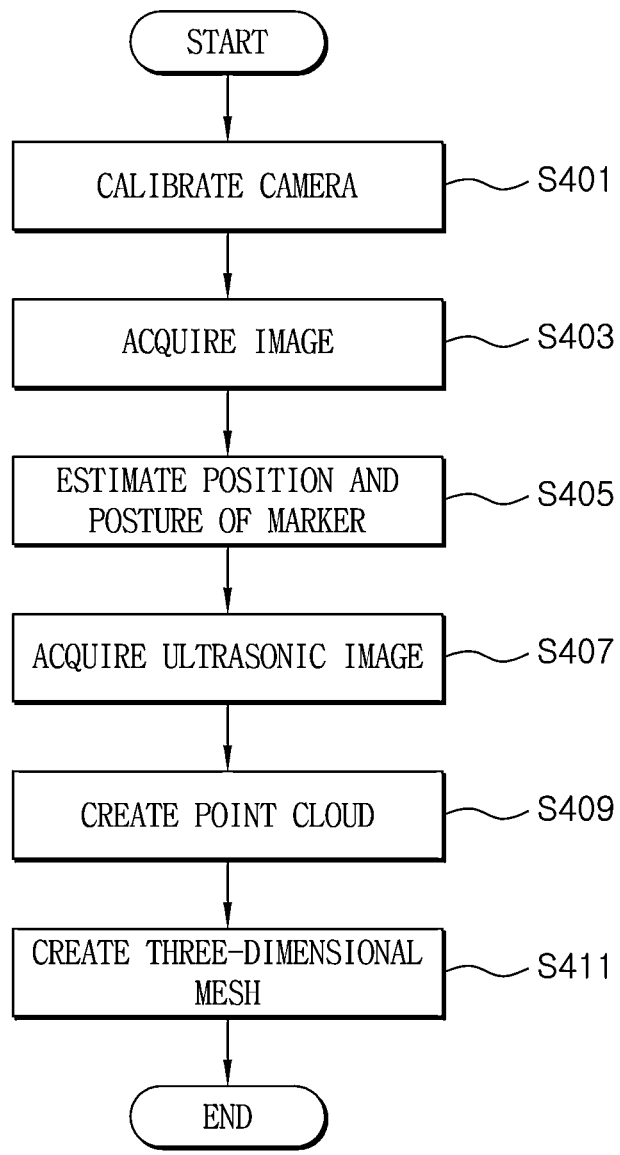
FIG. 2 is a flowchart illustrating an ultrasonic image presentation method according to an embodiment of the present invention.

FIG. 2 is a flowchart illustrating an ultrasonic image presentation method according to an embodiment of the present invention.

Referring to FIG. 2, first, camera calibration of the photographing unit 200 is performed (S401). According to the present invention, camera calibration is performed for recognizing internal information, position relationship, and the like of the marker tracking camera depending on whether the photographing unit is a single camera or a multi-camera set.

The ultrasonic image presentation unit 300 estimates the position and posture of the marker 120 in the three-dimensional image from the image taken by the photographing unit 200 (S403, S405).

The ultrasonic image presentation unit 300 estimates the position and posture of the probe in the three-dimensional image from the estimated position and posture information of the marker.

The ultrasonic image presentation unit 300 acquires an ultrasonic image, which is a two-dimensional depth cross-sectional image for a part coming into contact with the probe 110 of the ultrasonic scanner 100 (S407).

The ultrasonic image presentation unit 300 creates a point cloud by converting pixels of the ultrasonic image into points of a three-dimensional image from the estimated information on the position and posture of the probe 110 (S409).

The ultrasonic image presentation unit 300 creates a three-dimensional mesh from the point cloud created on the basis of the point information of the three-dimensional image created as the probe 110 moves. In addition, the three-dimensional image is restored on the basis of the created three-dimensional ultrasonic mesh (S411).

The ultrasonic image presentation unit 300 restores the three-dimensional ultrasonic image on the basis of the created point cloud to allow the display unit 400 to display the restored three-dimensional ultrasonic image.

Figure 3:
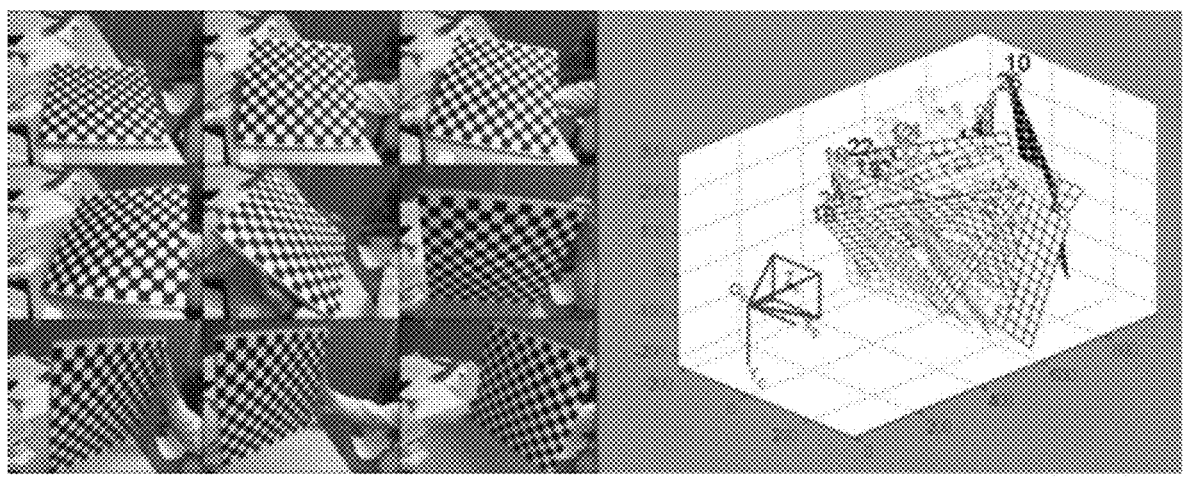
FIGS. 3 and 4 are diagrams illustrating a camera calibration process according to an embodiment of the present invention.
Figure 4:
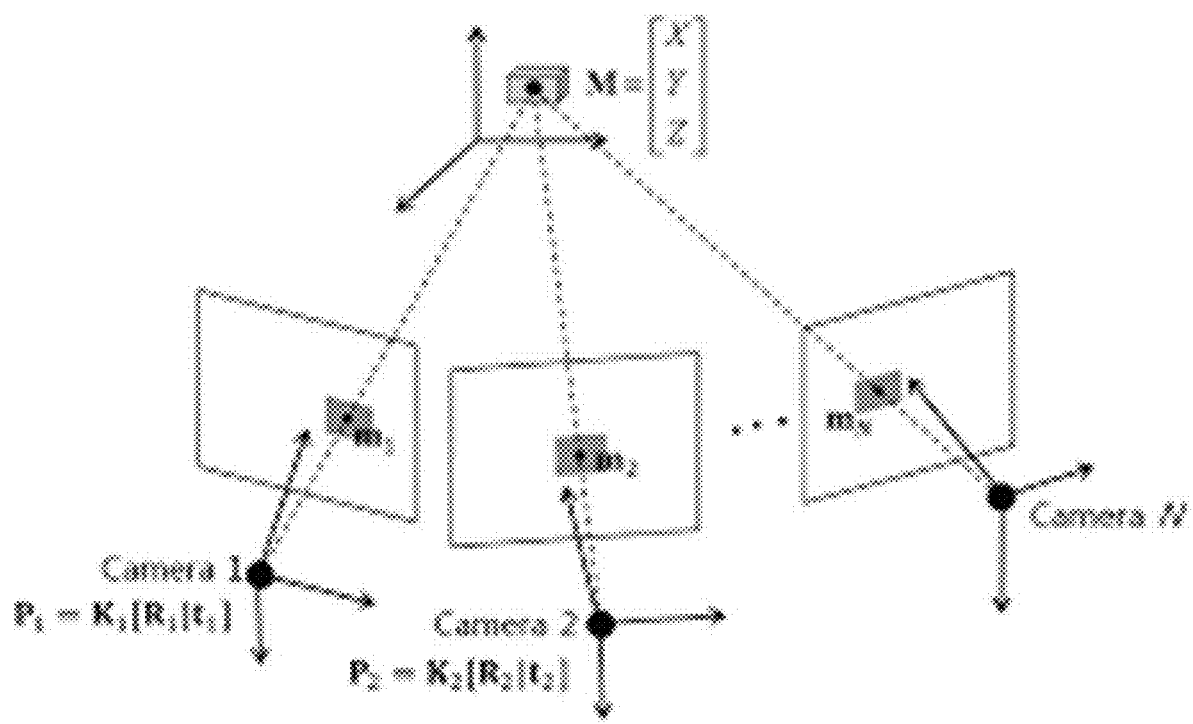

FIGS. 3 and 4 are diagrams illustrating a camera calibration process according to an embodiment of the present invention.

FIG. 3 is a diagram illustrating a calibration process of a single camera. Referring to FIG. 3, in the case of a single camera, a camera calibration process is performed to accurately recognize a relationship between the actual three-dimensional position of the subject taken by the camera and the two-dimensional position on the photograph.

First, a calibration board that can detect points arranged at regular intervals is photographed several times, and various unique values of the camera (such as a focal length, a main point, and a lens distortion coefficient) are extracted from the calibration board. Once the unique values of the camera are extracted, they do not change. Therefore, the calibration process may be performed only once.

FIG. 4 is a diagram illustrating a multi-camera set calibration process. Referring to FIG. 4, in the case of a multi-camera set, a single camera calibration process is performed for each and every camera, and a process of finally extracting a positional relationship between the cameras is performed.

First, after a plurality of cameras photograph a single subject at the same time, the movement and rotation values between the cameras are obtained using the same point information on the photographed two-dimensional image.

In the case of a multi-camera set, it is necessary to perform the calibration process whenever the relative positions and angles of the cameras change. However, if the cameras are all fixed, it is necessary to perform the calibration only once for the first time.

FIG. 5 illustrates a single camera and a two-dimensional image marker according to an embodiment of the present invention.

Referring to FIG. 5, as an example of the case of a single camera and a rectangular two-dimensional image marker, a rectangular two-dimensional image marker is searched from the image acquired from the single camera, and the position and posture of the marker are recognized. For example, the position and posture of the rectangular two-dimensional image marker may be estimated as X: 50 mm, Y: 30 mm, Z: 400 mm, pitch: 40, yaw: 50, and roll: 20. In this case, any method well known in the art may be used to recognize the position and posture of the marker.

FIG. 6 illustrates a multi-camera set and a bar type marker according to another embodiment of the present invention.

Referring to FIG. 6, as an example of the multi-camera set and the bar type marker, the position and posture of the marker may be recognized by searching for the bar type marker from the image acquired from the multi-camera set. The position and posture of the bar type marker may be estimated through a three-dimensional restoration method.

As shown in FIG. 6, the bar type marker 120 may be formed on the rear surface of the ultrasonic scanner 100 in the longitudinal direction. More specifically, the probe may be formed on the front surface of the ultrasonic scanner 100, and the bar type marker 120 may be formed on the rear surface opposite to the front surface of the ultrasonic scanner 100 in the longitudinal direction. In order to restore the ultrasonic image, it is necessary to recognize a rotation component of the ultrasonic scanner 100. Therefore, not only the line segment formed in the longitudinal direction, but also an additional line segment (short line segment shown in FIGS. 6 and 7) formed perpendicular to the longitudinal line segment is added. Using information on only one three-dimensional line segment, the position and inclination of the line segment can be estimated. However, it is difficult of estimate the Y-axis rotation component (referred to as "yaw rotation component"). In order to restore the ultrasonic image, yaw rotation component information is required. Therefore, an "L" shape rather than a straight line shape is used in the bar type marker 120. In this case, the shape of the bar type marker 120 may also be modified to another shape by which the Y-axis rotation component (yaw rotation component) of the ultrasonic scanner can be estimated. For example, a plurality of short line segments may be attached, or the short line segment may be formed in any shape other than the straight line.

Figure 7A:
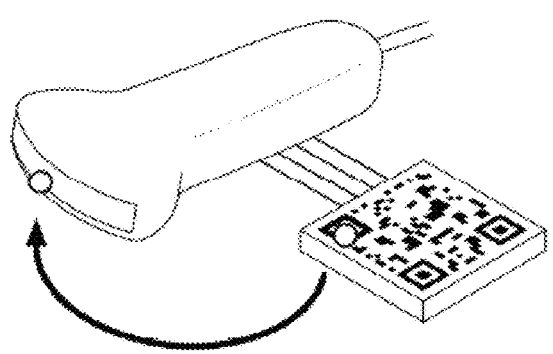
FIGS. 7($a$) and 7($b$) illustrate an ultrasonic scanner having the marker according to the present invention.
Figure 7B:
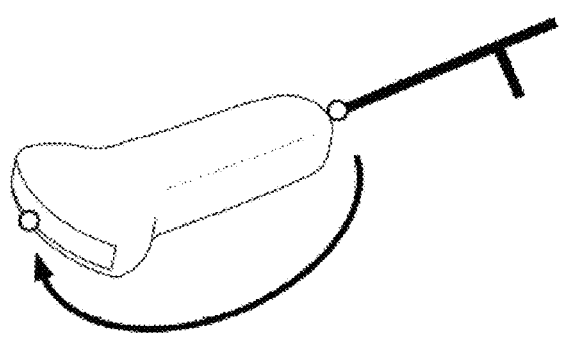

FIGS. 7(*a*) and 7(*b*) illustrate an ultrasonic scanner provided with a marker according to the present invention. FIG. 7(*a*) is an exemplary diagram illustrating a two-dimensional image marker, and FIG. 7(*b*) is an exemplary diagram illustrating a bar type marker.

As shown in FIGS. 7(*a*) and 7(*b*), the three-dimensional position and posture of the probe 110 may be estimated using the relationship between the marker 120 and the probe 110 measured in advance according to the present invention.

Figure 8:
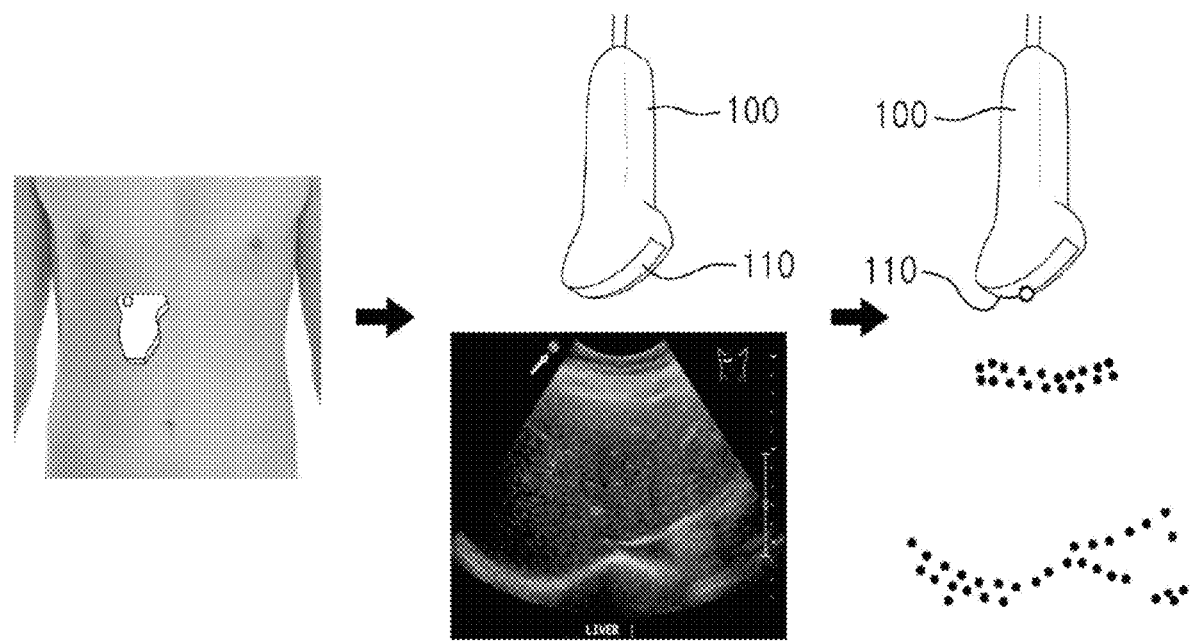
FIG. 8 illustrates an ultrasonic image acquirement and three-dimensional point cloud creation process according to an embodiment of the present invention.

FIG. 8 illustrates an ultrasonic image acquisition and three-dimensional point cloud creation process according to an embodiment of the present invention.

Referring to FIG. 8, after acquiring a depth cross-sectional image from the probe 110, points having a brightness higher than a certain level among pixels in the image are restored in the three-dimensional form using the position and posture information of the probe 110. In this case, since the probe 110 moves in real time, information on numerous three-dimensional points can be obtained for every unit time.

Figure 9:
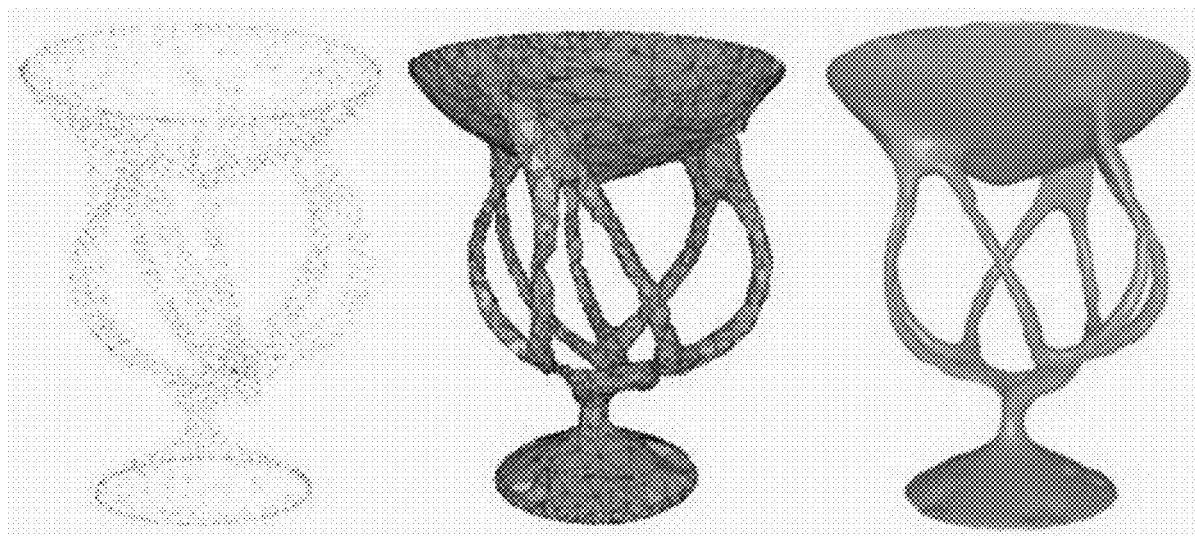
FIG. 9 illustrates a process of creating a three-dimensional mesh from a point cloud according to an embodiment of the present invention.

FIG. 9 illustrates a process for creating a three-dimensional mesh from the point cloud according to an embodiment of the present invention.

As shown in FIG. 9, the ultrasonic image creation device according to the present invention may create a mesh by connecting the information on the three-dimensional points from the point cloud.

Figure 10:
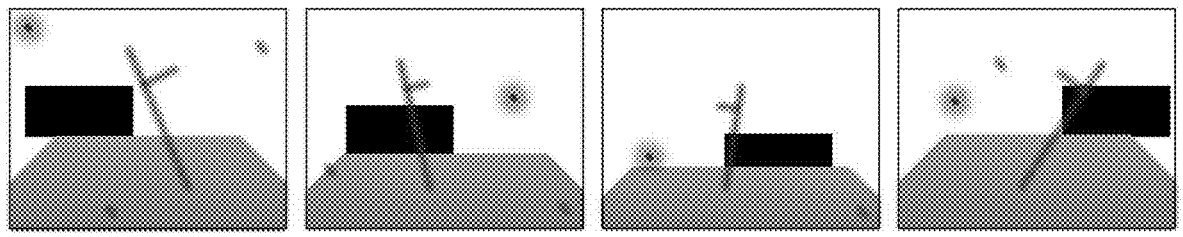
FIG. 10 is a diagram for explaining a bar type marker tracking image acquirement operation according to an embodiment of the present invention.

FIG. 10 is a diagram for explaining a bar type marker tracking image acquisition operation according to an embodiment of the present invention. FIG. 10 illustrates that the tracking multi-camera set 200 has four cameras, and the images photographed by each camera are shown as four image screens.

Referring to FIG. 10, all the images photographed by each camera are acquired in real time for every frame.

Figure 11:
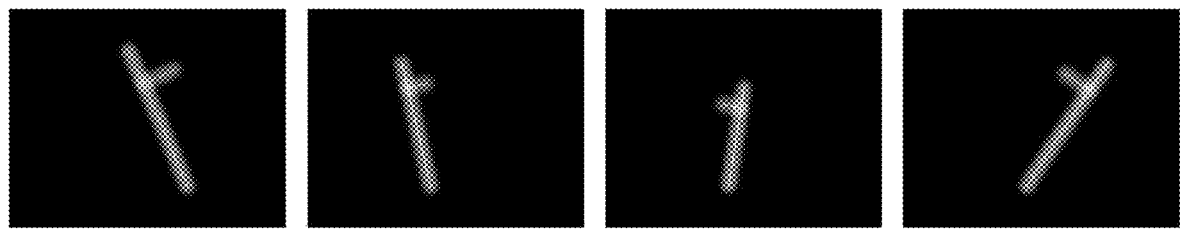
FIG. 11 is a diagram for explaining an image refining operation according to an embodiment of the present invention.

FIG. 11 is a diagram for explaining an image refining operation according to an embodiment of the present invention.

Referring to FIG. 11, the bar type marker is separated for each camera from the acquired image (for example, in the case of a bar type marker such as a laser marker, the bar (laser) color range of each bar (laser) line segment is separated), and unnecessary noise components smaller than a certain area are removed as many as possible.

Figure 12:
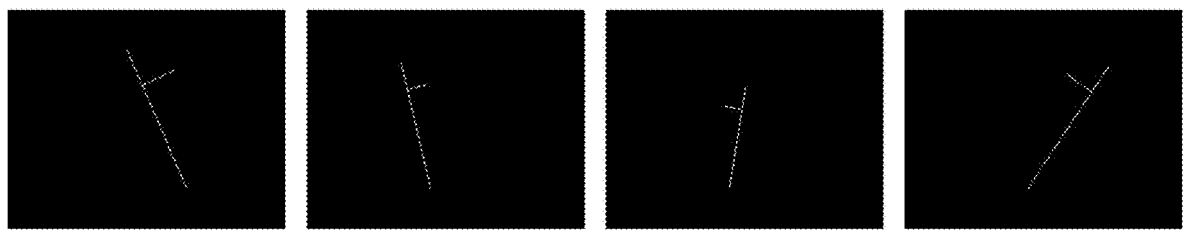
FIG. 12 is a diagram for explaining a two-dimensional optimum line segment search operation according to an embodiment of the present invention.

FIG. 12 is a diagram for explaining a two-dimensional optimum line segment search operation according to an embodiment of the present invention.

Referring to FIG. 12, in the two-dimensional optimum line segment search process for each image, an optimum line segment is searched by using a statistically robust line fitting algorithm. In this case, as the line fitting algorithm, any algorithm well known in the art may be employed, such as a Inui, Meer, Rousseeuw, and the like.

Figure 13:
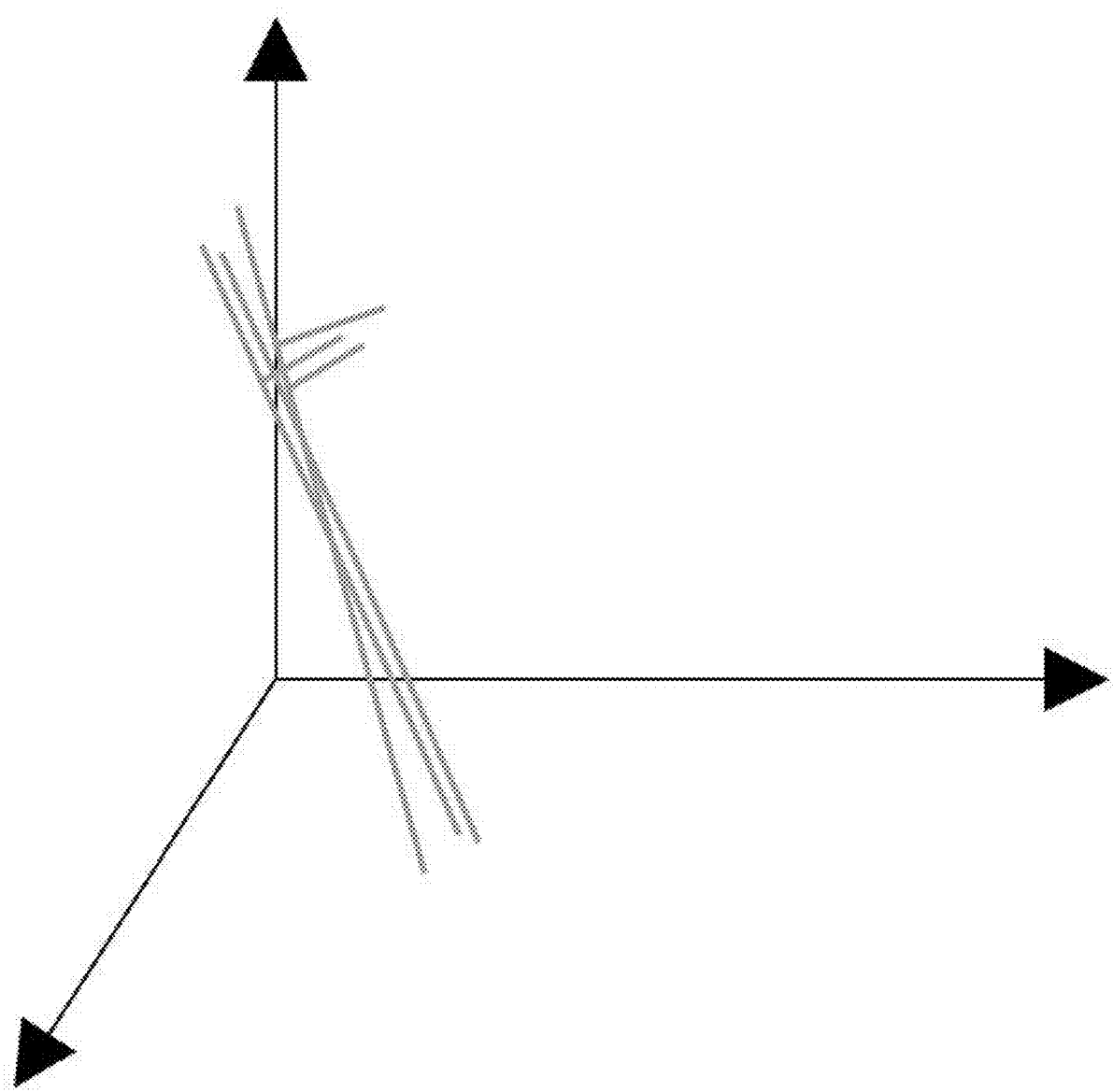
FIG. 13 is a diagram for explaining a three-dimensional line segment restoration operation according to an embodiment of the present invention.
Figure 14:
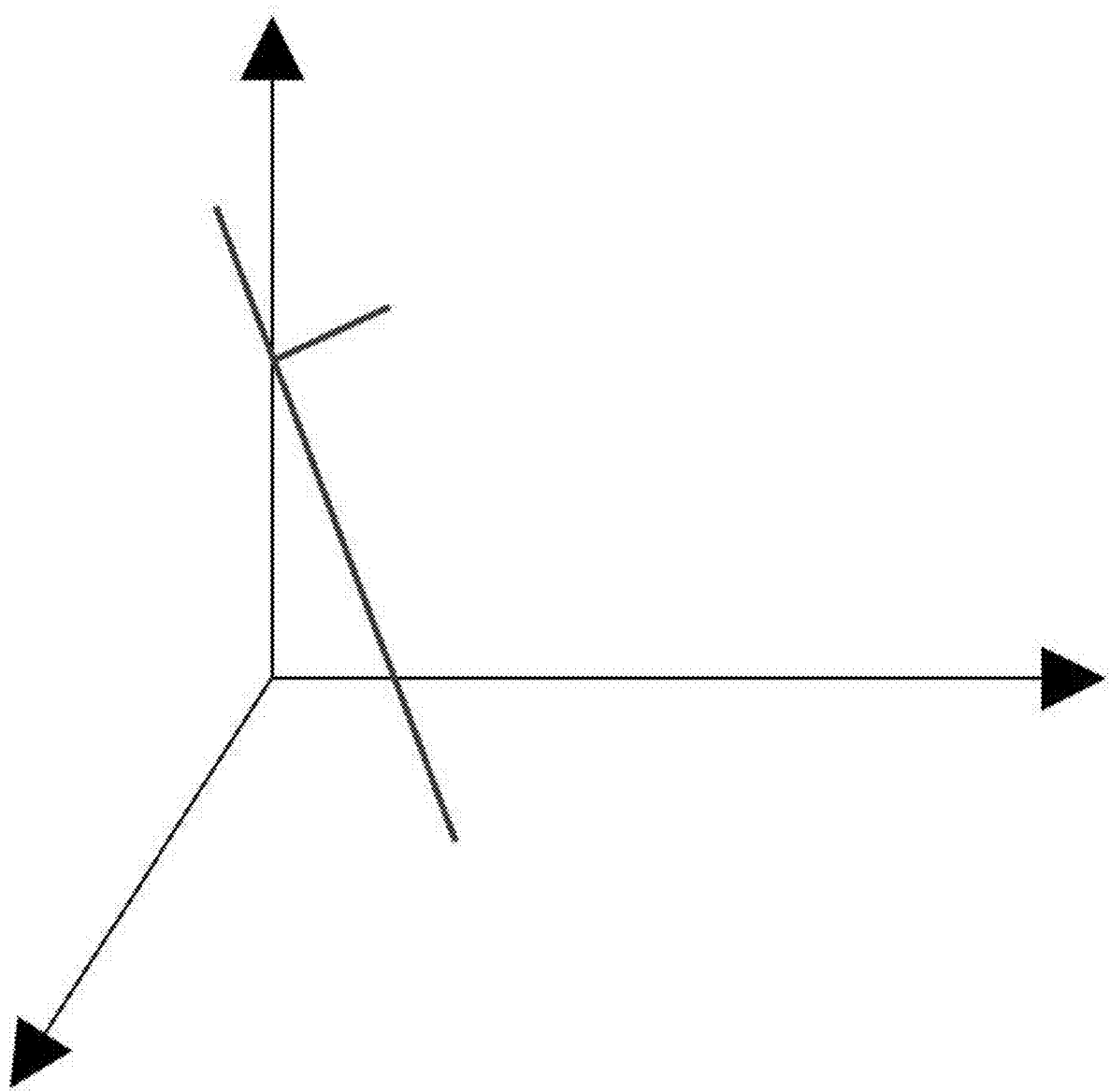
FIG. 14 is a diagram for explaining a two-dimensional optimum line segment search operation according to an embodiment of the present invention.

FIG. 13 is a diagram for explaining a three-dimensional line segment restoration operation according to an embodiment of the present invention. FIG. 14 is a diagram for explaining a three-dimensional optimum line segment search operation according to an embodiment of the present invention. That is, FIGS. 13 and 14 are diagrams for exemplarily explaining an optimum three-dimensional line segment restoration operation according to an embodiment of the present invention.

Referring to FIGS. 13 and 14, through the three-dimensional line segment restoration operation, it is possible to restore the optimal three-dimensional line segment by using the two-dimensional line segment information and the position relationship information between the cameras recognized in advance. FIG. 14 illustrates the restored optimum three-dimensional line segment.

Referring to FIG. 13, in the three-dimensional line segment restoration operation, the two-dimensional line segment information is bound on a predetermined number basis (for example, two by two). Then, a plurality of three-dimensional line segments can be restored by using the position relationship information between the cameras recognized in advance. FIG. 13 illustrates the three-dimensional line segments.

Referring to FIG. 14, in the three-dimensional optimum line segment search process, the optimum three-dimensional line segments can be found by performing the line fitting again for the information on both endpoints of a plurality of three-dimensional line segments. In this case, any algorithm well known in the art may be employed as the line fitting algorithm.

Figure 15:
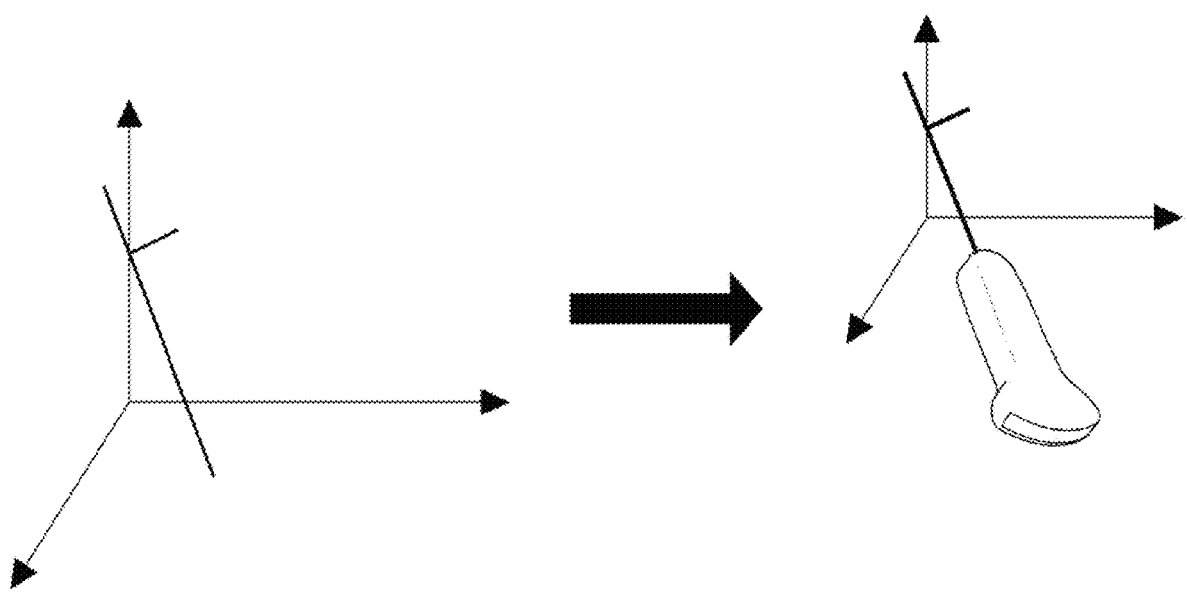
FIG. 15 is a diagram for explaining a medical tool posture estimation process according to an embodiment of the present invention.

FIG. 15 is a diagram for explaining a medical tool posture estimation process according to an embodiment of the present invention.

Referring to FIG. 15, in the medical tool posture estimation process, the actual medical tool three-dimensional posture may be estimated by using the position relationship between the medical tool and the bar type marker measured in advance. For example, the three-dimensional posture of a body part of the medical tool may be estimated by using the position relationship between the bar type marker line segment and the medical tool (probe of the ultrasonic scanner). In this case, if the position and length of the bar type marker line segment are accurately estimated, the position and posture of the medical tool (ultrasonic scanner probe) can be automatically and accurately estimated.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

What is claimed is:

1. An ultrasonic image presentation device comprising:
an ultrasonic scanner having a probe which is a part coming into direct contact with an object and a marker;
a photographing unit configured to photograph the marker;
an ultrasonic image presentation unit configured to acquire an ultrasonic image as a two-dimensional depth cross-sectional image for a part coming into contact with the probe of the ultrasonic scanner, estimate a position and posture of the marker in a three-dimensional image on the basis of an image photographed by the photographing unit; estimate a position and posture of the probe in the three-dimensional image from the estimated marker position and posture information, create a point cloud by converting pixels of the ultrasonic image into points of the three-dimensional image on the basis of the estimated probe position and posture information, and restore the three-dimensional ultrasonic image on the basis of the created point cloud; and
a display unit configured to display the three-dimensional ultrasonic image restored by the ultrasonic image presentation unit,
wherein the ultrasonic image presentation unit estimates the position and posture of the probe by using the position and posture information of the marker and information on a relative distance and a relative angle between the marker and the probe measured in advance.

2. The ultrasonic image presentation device according to claim 1, wherein the ultrasonic image presentation unit creates a three-dimensional mesh from the point cloud created on the basis of information on points of the three-dimensional image created as the probe moves, and
the three-dimensional ultrasonic image is restored on the basis of the created three-dimensional mesh.

3. The ultrasonic image presentation device according to claim 2, wherein the photographing unit includes a single camera,
the marker is a two-dimensional image marker, and
the ultrasonic image presentation unit searches for the two-dimensional image marker from the image photographed by the single camera and estimates the position and posture of the two-dimensional image marker.

4. The ultrasonic image presentation device according to claim 2, wherein the photographing unit includes a multi-camera set having a plurality of cameras provided in a plurality of places,
the marker is a bar type marker formed in a bar shape, and
the ultrasonic image presentation unit searches for the bar type marker from the images photographed by the multi-camera set and estimates the position and posture of the bar type marker.

5. The ultrasonic image presentation device according to claim 2, wherein the ultrasonic image presentation unit creates a point cloud by converting pixels of the ultrasonic image into points of a three-dimensional image depending on a relative distance from the position of the probe.

6. An ultrasonic image presentation method using an ultrasonic image presentation device provided with an ultrasonic scanner having a probe which is a part coming into direct contact with an object and a marker, a photographing unit for photographing the marker, an ultrasonic image presentation unit, and a display unit, the method comprising:
- acquiring an ultrasonic image which is a two-dimensional depth cross-sectional image for a part coming into contact with the probe of the ultrasonic scanner;
- estimating a position and posture of the marker in a three-dimensional image on the basis of the image photographed by the photographing unit;
- estimating a position and posture of the probe in the three-dimensional image on the basis of the estimated position and posture information of the marker;
- creating a point cloud by converting pixels of the ultrasonic image into points of the three-dimensional image on the basis of the estimated position and posture information of the probe; and
- restoring the three-dimensional ultrasonic image on the basis of the created point cloud and displaying the restored three-dimensional ultrasonic image on the display unit,
- wherein the ultrasonic image presentation unit estimates the position and posture of the probe by using position and posture information of the marker and information on a relative distance and a relative angle between the marker and the probe measured in advance.

7. The ultrasonic image presentation method according to claim 6, wherein the ultrasonic image presentation unit creates a three-dimensional mesh from a point cloud created from information on points of the three-dimensional image created as the probe moves, and the three-dimensional ultrasonic image is restored on the basis of the created three-dimensional mesh.

8. The ultrasonic image presentation method according to claim 7, wherein the photographing unit includes a single camera,
- the marker is a two-dimensional image marker, and
- the ultrasonic image presentation unit searches for the two-dimensional image marker from the image photographed by the single camera and estimates the position and posture of the two-dimensional image marker.

9. The ultrasonic image presentation method according to claim 7, wherein the photographing unit includes a multi-camera set provided with a plurality of cameras placed in a plurality of positions,
- the marker is a bar type marker formed in a bar shape, and
- the ultrasonic image presentation unit searches for the bar type marker from the images photographed by the multi-camera set and estimates the position and posture of the bar type marker.

10. The ultrasonic image presentation method according to claim 7, wherein the ultrasonic image presentation unit creates a point cloud by converting pixels of the ultrasonic image into points of a three-dimensional image depending on a relative distance from the position of the probe.

\* \* \* \* \*